United States Patent [19]

Thomas, Jr. et al.

[11] Patent Number: 5,919,463
[45] Date of Patent: Jul. 6, 1999

[54] CLOSTRIDIUM DIFFICLE TOXINS AS MUCOSAL ADJUVANTS

[75] Inventors: William D. Thomas, Jr., Winchester; Thomas P. Monath, Harvard; Zhenxi Zhang, Cambridge, all of Mass.; Francisco Javier Torres-Lopez, San Clemente, Mexico; Wende Lei, Cambridge, Mass.; David M. Lyerly, Radford; James S. Moncrief, Christiansburg, both of Va.

[73] Assignee: OraVax, Inc., Cambridge, Mass.

[21] Appl. No.: 08/543,708

[22] Filed: Oct. 16, 1995

Related U.S. Application Data

[63] Continuation-in-part of application No. 08/499,384, Jul. 7, 1995, abandoned.

[51] Int. Cl.$^6$ .......................... A61K 39/08; A61K 38/46
[52] U.S. Cl. ................. 424/239.1; 424/94.6; 424/278.1; 424/184.1; 424/192.1; 424/236.1; 424/247.1; 424/234.1; 530/300; 530/350; 530/825; 514/2
[58] Field of Search .............................. 424/184.1, 192.1, 424/236.1, 239.1, 247.1, 234.1, 94.6, 278.1; 530/300, 350, 825; 514/2

[56] References Cited

U.S. PATENT DOCUMENTS

| | | | |
|---|---|---|---|
| 4,713,240 | 12/1987 | Wilkins et al. | 424/92 |
| 4,863,852 | 9/1989 | Wilkins et al. | 435/7 |
| 5,098,826 | 3/1992 | Wilkins et al. | 435/7.32 |
| 5,182,109 | 1/1993 | Tamura et al. | 424/92 |

FOREIGN PATENT DOCUMENTS

| | | |
|---|---|---|
| 0 154 064 A1 | 9/1985 | European Pat. Off. . |
| 0 553 444 A1 | 8/1993 | European Pat. Off. . |
| WO 94/02173 | 2/1994 | WIPO . |
| 9413264 | 6/1994 | WIPO . |
| WO 94 21684 A | 9/1994 | WIPO . |

OTHER PUBLICATIONS

Bartoloni, et al., "Immunogenicity of meningococcal B polysaccharide conjugated to tetanus toxoid or CRM197 via adipic acid dihydrazide", Vaccine 13:463–470 (1995).

Davin et al., *H. pylori* Urease Elicits Protection Against *H. felis* Infection in Mice, Gastroenterology 104:A1035 (Apr. 1993).

Pallen and Clayton, Vaccination Against *Helicobacter pylori* Urease, The Lancet 336:186–187, 1990.

Allo et al., Prevention of Clindamycin–Induced Colitis in Hamsters by *Clostridium sordellii* Antitoxin, Gastroenterology 76:351–355, 1979.

Almeida et al., Immune Response to Nasal Delivery of Antigenically Intact Tetanus Toxoid Associated with Poly(L–lactic acid) Microspheres in Rats, Rabbits and Guinea–pigs, J. Pharm. Pharmacol. 45:198–203, 1993.

Barroso et al., Mutagenesis of the *Clostridium difficile* Toxin B Gene and Effect on Cytotoxic Activity, Microbial. Pathogenesis 16:297–303, 1994.

Barroso et al., Nucleotide Sequence of *Clostridium difficile* Toxin B Gene, Nucleic Acids Research 18:4004, 1990.

Bette et al., A Comparative Biochemical, Pharmacological and Immunological Study of *Clostridium Novyi* α–Toxin, *C. Difficile* Toxin B and *C. Sordellii* Lethal Toxin, Toxicon 29:877–887, 1991.

Budai, Intestinal Infections: Current Aspects and New Possibilities of Prophylaxis and Treatment, Ther. Hung. (Hungary) 37(1):3–16, 1989.

Burnette et al., Site–Specific Mutagenesis of the Catalytic Subunit of Cholera Toxin: Substituting Lysine for Arginine 7 Causes Loss of Activity, Infection and Immunity 59:4266–4270, 1991.

Corthier et al., Protection Against Experimental Pseudomembranous Colitis in Gnotobiotic Mice by Use of Monoclonal Antibodies Against *Clostridium difficile* Toxin A, Infection and Immunity 59:1192–1195, 1991.

Cryz Jr. et al., Human Immunodeficiency Virus–1 Principal Neutralizing Domain Peptide–toxin A conjugate Vaccine, Vaccine 13:67–71, 1995.

Czerkinsky et al., Oral Administration of a Streptococcal Antigen Coupled to Cholera Toxin B Subunit Evokes Strong Antibody Responses in Salivary Glands and Extramucosal Tissues, Infection & Immunity 57:1072–77, 1989.

Daubener et al., *Clostridium difficile* Toxins A and B Inhibit Human Immune Response In Vitro, Infection and Immunity 56:1107–1112, 1988.

Dellert and Cohen, Diarrheal Disease Established Pathogens, New Pathogens, and Progress in Vaccine Development, Pediatric Gastroenterology 23:637–654, 1994.

Dove et al., Molecular Characterization of the *Clostridium difficle* Toxin A Gene, Infection and Immunity 58:480–488, 1990.

Dubos et al., Immediate Postnatal Inoculation of a Microbial Barrier to Prevent Neonatal Diarrhea Induced by *Clostridium difficile* in Young Conventional and Gnotobiotic Hares, Am. J. Vet. Res. 45:1242–1244, 1984.

Fernie et al., Active and Passive Immunization to Protect Against Antibiotic Associated Caecitis in Hamsters, Develop. biol. Standard 53:325–332, 1983.

Field et al., Intestinal Electrolyte Transport and Diarrheal Disease, New England Journal of Medicine 321:879–883, 1989.

(List continued on next page.)

*Primary Examiner*—Paula K. Hutzell
*Assistant Examiner*—Khalid Masood
*Attorney, Agent, or Firm*—Clark & Elbing LLP

[57] ABSTRACT

The invention features methods and compositions for inducing protective and/or therapeutic immune responses to an antigen in a mammal. In these methods, an antigen is administered to the mammal with a toxin of a Clostridium (e.g., *C. difficile*), or a fragment or derivative thereof having adjuvant activity.

21 Claims, 9 Drawing Sheets

OTHER PUBLICATIONS

Flegel et al., Cytokine Response by Human Monocytes to *Clostridium difficile* Toxin A and Toxin B, Infection and Immunity 59:3659–3666, 1991.

Frey and Wilkins, Localization of Two Epitopes Recognized by Monoclonal Antibody PCG–4 on *Clostridium difficile* Toxin A, Infection and Immunity 60:2488–2492, 1992.

Gordon and Leppla, Proteolytic Activation of Bacterial Toxins: Role of Bacterial and Host Cell Proteases, Infect. Immun. 62:333–340, 1994.

Grant et al., Role of Trypsin–Like Cleavage at Arginine 192 in the Enzymatic and Cytotonic Activities of *Escherichia coli* Heat–Labile Enterotoxin, Infect. Immun. 62:4270–4278, 1994.

Holmgren et al., Cholera toxin and cholera B subunit as oral–mucosal adjuvant and antigen vector systems, Vaccine 11:1179–1183, 1993.

Kim et al., Immunization of Adult Hamsters against *Clostridium difficile*–Associated Ileocecitis and Transfer of Protection to Infant Hamsters, Infect. Immun. 55:2984–2992, 1987.

Liang et al., Oral Administration of Cholera Toxin–Sendai Virus Conjugate Potentiates Gut and Respiratory Immunity Against Sendai Virus, J. Immunol. 141:1495–1501, 1988.

Libby et al., Effects of the Two Toxins of *Clostridium difficile* in Antibiotic–Associated Cecitis in Hamsters, Infect. Immun. 36:822–829, 1982.

Lyerly et al., Vaccination against Lethal *Clostridium difficile* Enterocolitis with a Nontoxic Recombinant Peptide of Toxin A, Current Microbiology 21:29–32, 1990.

Malorni et al., Enhancement of Cell–Mediated Cytotoxicity by *Clostridium Difficile* Toxin A: An In Vitro Study, Toxicon 29:417–428, 1991.

McGhee and Kiyono, New Perspectives in Vaccine Development: Mucosal Immunity to Infections, Infectious Agents and Disease 2:55–73, 1993.

McGhee et al., The mucosal immune system: from fundamental concepts to vaccine development, Vaccine 10:75–88, 1992.

Okamoto et al., Effect of Substitution of Glycine for Arginine at Position 146 of the A1 Subunit on Biological Activity of *Escherichia coli* Heat–Labile Enterotoxin, J. Bacteriology 170:2208–2211, 1988.

Pothoulakis et al., *Clostridium difficile* Toxin A Stimulates Intracellular Calcium Release and Chemotactic Response in Human Granulocytes, J. Clin. Invest. 81:1741–1745, 1988.

Price et al., Cloning of the Carbohydrate–binding Portion of the Toxin A Gene of *Clostridium difficile,* Current Microbiology 16:55–60, 1987.

Sansonetti, *Escherichia coli,* Shigella, antibiotic–associated diarrhea, and prevention and treatment of gastroenteritis, Current Opinion in Infect. Diseases 5:66–73, 1992.

Siffert et al., Effects of *Clostridium difficile* Toxin B on Human Monocytes and Macrophages: Possible Relationship with Cytoskeletal Rearrangement, Infect. Immun. 61:1082–1090, 1993.

Silva, Update on Pseudomembranous Colitis, West J. Med. 151:644–648, 1989.

Spangler, Structure and Function of Cholera Toxin and the Related *Escherichia coli* Heat–Labile Enterotoxin, Microbiological Reviews 56:622–647, 1992.

Tamura et al., *Escherichia coli* heat–labile enterotoxin B subunits supplemented with a trace amount to the holotoxin as an adjuvant for nasal influenza vaccine, Vaccine 12:1083–1089, 1994.

Trnka and Lamont, *Clostridium difficile* Colitis, Advances in Internal Medicine 29:85–107, 1984.

Xu–Amano et al., Helper T Cell Subsets for Immunoglobulin A Responses: Oral Immunization with Tetanus . . . Induces Th2 Cells in Mucosa Associated Tissues, J. Exp. Med. 178:1309–1320, 1993.

Lee et al., Oral Immunization with Recombinant *Helicobacter pylori* Urease Induces Secretory IgA Antibodies and Protects Mice from Challenge with *Helicobacter felis,* J. Infectious Disease 172:161–172, 1995.

Lyerly et al., Purification and Properties of Toxins A and B of *Clostridium difficile,* FEMS Microbiology Letters 33:31–35, 1986.

Michetti et al. (1994) Gastroenterology. vol. 107, 1002–1011.

Holmgren et al. (1994) Am. J. Trop. Med. Hyg. vol. 50(5) Suppl. 42–54.

Torres et al. (1995) Infection and Immunity. vol. 63(12)4619–4627.

CLOSTRIDIUM DIFFICILE TOXINS AS MUCOSAL ADJUVANTS

This application is a continuation-in-part of U.S. Ser. No. 08/499,384, (abandoned) filed on Jul. 7, 1995.

BACKGROUND OF THE INVENTION

This invention relates to mucosal adjuvants.

*Clostridium difficile* is a gram-positive, spore-forming, toxigenic bacterium that causes antibiotic-associated diarrhea which can progress into severe and sometimes fatal colitis. Upon disruption of the normal intestinal flora by, e.g., antibiotic or anti-neoplastic therapy, *C. difficile* may become established in the colon and produce two high molecular weight toxins, Toxin A and Toxin B. Both of these polypeptides are cytotoxins, but Toxin B is greater than 1000-fold more potent than Toxin A. Toxin A is also an enterotoxin, causing accumulation of fluid in ligated animal intestinal loops.

SUMMARY OF THE INVENTION

We have shown that *C. difficile* toxins, when administered intranasally with an antigen (e.g., *Helicobacter pylori* urease, ovalbumin (OVA), or keyhole limpet hemocyanin (KLH)) are effective in inducing mucosal immune responses to the antigen. For example, the immune response to *H. pylori* urease induced upon intranasal administration of urease with a *C. difficile* toxin is protective against Helicobacter infection. We have also shown that intranasal administration of an antigen with a non-toxic derivative of *C. difficile* Toxin A, containing the carboxyl-terminal repeats which make up the carbohydrate binding domain, leads to a mucosal immune response. In addition, we have shown that rectal and vaginal immunization routes are effective. Thus, *C. difficile* toxins, and fragments thereof, are effective mucosal adjuvants which can be used in vaccination methods.

Accordingly, the invention features a method of inducing an immune response (e.g., a mucosal immune response) to an antigen in a mammal. In this method, the antigen is administered to the mammal with a toxin (e.g., *C. difficile* Toxins A or B), or a fragment or derivative thereof having adjuvant activity (e.g., a carboxyl-terminal fragment containing some or all of the repeats which make up the carbohydrate binding domain of Toxin A (ARU; see below)), from a bacterium of the genus Clostridium (e.g., *C. difficile, C. novyi, C. sordellii, C. perfringens, C. tetani*, and *C. botulinum*). The toxins may be administered individually with an antigen or in combinations (e.g., antigen+Toxin A+Toxin B). The method of the invention may be carried out in order to prevent or decrease the chances of a future infection (i.e., to induce a protective immune response) and/or to treat an ongoing infection (i.e., to induce a therapeutic immune response).

An "adjuvant," as is used herein, is a material that, when administered with an antigen, increases an immune response to the antigen. A "toxin," as is used herein, is a noxious or poisonous substance (e.g., a cytotoxin) that is formed or elaborated either as an integral part of a cell or tissue (endotoxin), as an extracellular product (exotoxin), or as a combination thereof, during the metabolism and growth of certain microorganisms and higher plant and animal species.

The toxins used in the invention may be purified from bacterial cultures (e.g., cultures of *C. difficile*, see, e.g., Lyerly et al., FEMS Microbio. Lett. 33:31–35, 1986), or produced using standard recombinant or chemical synthetic methods. A polypeptide is described as "recombinant" if it is made using methods of recombinant DNA technology, e.g., by expression of a nucleic acid encoding the polypeptide in, e.g., a heterologous bacterium, yeast, or mammalian cell. The nucleic acid encoding the polypeptide is contained within a vector, or, alternatively, is integrated into a chromosome in the cell in which it is expressed (see, e.g., Ausubel et al., Eds., Current Protocols in Molecular Biology, John Wiley & Sons, Inc., 1994). A protein is described as "synthetic" if it is made in vitro using chemical methods, e.g., standard solid phase peptide synthesis. Toxin fragments may be made using, e.g., recombinant, synthetic, or proteolytic methods. Generally, for peptide toxins, fragments should be at least 20 amino acids in length. Particularly useful fragments may contain all or some of the carboxyl-terminal repeats which make up the carbohydrate binding region of Toxin A. Derivatives of the toxins included in the invention may contain mutations of, insertions into, and/or deletions of the wild-type toxin sequences, provided that adjuvant activity is retained.

One skilled in the art will readily understand that in making fragments or derivatives of toxins for use in the methods and compositions of the invention, the requirements for maintenance of adjuvant activity are less stringent than for maintenance of biological activity. In fact, in making fragments and derivatives of the toxins of the invention, it is undesirable to maintain the biological activity (i.e., the toxicity) of the toxin.

The toxins used in the invention may also be produced as fusion proteins. A fusion protein is a polypeptide containing amino acid sequences corresponding to two or more proteins (or fragments thereof), which are normally separate proteins, linked together by a peptide bond(s). Fusion proteins generally are synthesized by expression of a hybrid gene containing nucleotides encoding each of the individual polypeptides which make up the fusion protein. An example of a fusion protein included in the invention is one which contains a Clostridium (e.g., *C. difficile*) toxin (e.g., *C. difficile* Toxin A or B; or a fragment or derivative thereof having adjuvant activity) fused to an antigen, e.g., *H. pylori* urease. Another type of fusion protein included in the invention consists of a *C. difficile* toxin fused to a polypeptide (e.g., glutathione S-transferase (GST)) which facilitates purification of the fusion protein. Toxins used in the invention may also be covalently coupled or chemically cross-linked to an antigen, using standard methods.

The invention may also employ Clostridium toxoids as adjuvants. A toxoid is a toxin (or mixture of toxins, e.g., *C. difficile* Toxin A and Toxin B) that has been treated so as to destroy or decrease the toxic properties of the toxin(s), but to retain antigenicity. Toxoids included in the invention are made using standard methods including, but not limited to, chemical (e.g., formaldehyde or glutaraldehyde) treatment, protease cleavage, and recombinant methods (e.g., by making fragments or mutations (e.g., point mutations) of the toxin(s)).

Any antigen to which a protective and/or therapeutic immune response is desired may be administered with an adjuvant of the invention. Exemplary organisms from which antigens (which may be, e.g., subunit antigens, killed whole cells, or lysates) may be derived include, but are not limited to, Helicobacters (e.g., *H. pylori, H. felis*, and *H. heilmanii*), Campylobacters (e.g., *C. jejuni*), Clostridia (e.g., *C. difficile*), *Corynebacterium diphtheriae, Bordetella pertussis*, influenza viruses, parainfluenza viruses, respiratory syncytial virus, *Borrelia burgdorferi*, Plasmodium, herpes simplex viruses, human immunodeficiency virus, papilloma viruses, *Vibrio cholera, Escherichia coli*, measles virus, rubella virus, varicella-zoster virus, mumps, rotavirus, shigella, *Salmonella typhi, Neisseria gonorrhoeae*, Yersinia, *Treponema pallidum*, hepatitis viruses, and Chlamydia. In addition, vaccines against nonmicrobial pathogens, e.g., vaccines containing killed cancer cells, or cancer cell-specific or enriched antigens, may be administered with the adjuvants of the invention.

The adjuvants (together with an antigen) of the invention are administered to a patient using standard methods. For example, administration may be to a mucosal (e.g., intranasal, oral, ocular, gastric, rectal, vaginal, intestinal, and urinary tract) surface of the patient. The compositions of the invention may also be administered by parenteral (e.g., intravenous, subcutaneous, intraperitoneal, or intramuscular) routes. Patients that may be treated using the method of the invention include, but are not limited to, mammals such as humans, cows, horses, pigs, dogs, cats, sheep, and goats.

The invention also features a composition containing an antigen and a toxin (or toxins) from a Clostridium (e.g., *C. difficile, C. novyi, C. sordellii, C. perfringens, C. tetani*, and *C. botulinum*), or a fragment or derivative thereof having adjuvant activity, in a pharmaceutically acceptable vehicle (e.g., water, a saline solution (e.g., phosphate-buffered saline), a bicarbonate solution (e.g., 0.24 M $NaHCO_3$), or in the form of a suppository, depending on the immunization route selected). Toxins which may be contained in the compositions of the invention are described above and include, e.g., *C. difficile* Toxin A, *C. difficile* Toxin B, both *C. difficile* Toxin A and *C. difficile* Toxin B, or fragments (e.g., a carboxyl-terminal fragment containing the repeats which make up the carbohydrate binding domain of Toxin A (ARU)) or derivatives thereof having adjuvant activity. The toxins may be recombinant, synthetic, part of a fusion protein (which includes, e.g., an antigen (e.g., *Helicobacter pylori* urease) or a polypeptide (e.g., GST) which facilitates purification of the fusion protein), covalently conjugated to an antigen, chemically cross-linked to an antigen, or toxoided (i.e., rendered less toxic, see above). Examples of antigens that may be contained with the adjuvants in the compositions of the invention are listed above.

The general concept of the use of bacterial toxins as mucosal adjuvants is not a new one. However, previously reported bacterial toxins with adjuvant activity represent a single class of closely related toxins, each consisting of multiple binding domain polypeptides and a single peptide having ADP-ribosyltransferase enzymatic activity. The mechanism of toxicity of these toxins involves a ribosylation of adenylate cyclase, which ultimately leads to a rise in the level of cAMP within the affected cell. Cholera toxin (CT) and the heat-labile toxin of *Escherichia coli* (LT) are classic examples of this class of adjuvants (Spangler et al., Microbiological Reviews 56(4):622–647, 1992), but pertussis toxin is also included in this group. Toxins A and B of *C. difficile* are much less well characterized than the ADP ribosylating toxins, but clearly represent a different class of toxins entirely in terms of mechanism of toxicity (e.g., *C. difficile* toxins induce cytoskeletal changes (see, e.g., Siffert et al., Infection and Immunity 61(3):1082–1090, 1993), while CT and LT promote ADP ribosylation (see, e.g., Spangler et al., supra)), enzymatic activity (*C. difficile* toxins do not have ADP-ribosyltransferase activity), and overall structure (*C. difficile* toxins are single polypeptide chains, while LT and CT each contain multiple chains). These differences are central to the mechanisms of adjuvancy, and probably affect critical aspects of the mucosal response.

Variables in the mucosal response include, but are not limited to, the effective dose of adjuvant, the inductive site relative to the effector site, T helper subsets involved, duration of antibody response, and memory of the immune response.

It is generally believed that intranasal administration of antigens gives rise to mucosal immune responses in the upper respiratory tract (URT; see, e.g., McGhee et al., Infections Agents and Disease 2:55–73, Raven Press, Ltd., New York, 1993). We have shown that, in addition to the URT, intranasal administration of antigens with Clostridium adjuvants (e.g., *C. difficile* Toxins A and B) gives rise to mucosal immune responses to the antigens in the gastrointestinal and genito-urinary tracts. Thus, an advantage of the adjuvants of the invention is that, upon intranasal administration, unlike traditional mucosal adjuvants (e.g., cholera toxin (CT)), the adjuvants of the invention can be used to induce immune responses in the intestinal and genito-urinary tracts. Accordingly, the adjuvants of the invention may be used when responses in these regions are central to inducing protection from, or in the treatment of, an infectious disease. In addition to the intranasal route, rectal or vaginal routes may be used. For example, the adjuvants of the invention may be used with appropriate vaccines in the prevention and treatment of sexually transmitted infectious diseases (e.g., Acquired Immunodeficiency Syndrome, gonorrhea, and chlamydia).

Other features and advantages of the invention will be apparent from the following description of the preferred embodiments thereof, and from the claims.

DETAILED DESCRIPTION

The drawings are first described.

Drawings

FIGS. 1A and 1B are graphs showing the levels of antigen-specific serum IgG, serum IgA, salivary IgA, fecal IgA, and vaginal IgA present in samples from mice intranasally immunized with ovalbumin (OVA; FIG. 1A) or Keyhole Limpet Hemocyanin (KLH; FIG. 1B), in combination with *C. difficile* Toxin A, *E. coli* heat-labile toxin (LT), or no adjuvant, as indicated in the figures.

Use of *C. difficile* Toxins as Mucosal Adjuvants

The invention provides methods and compositions for inducing protective and/or therapeutic immune responses to an antigen involving the use of a Clostridium (e.g., *C. difficile*) toxin polypeptide (e.g., *C. difficile* Toxin A or B), a fragment or derivative thereof having adjuvant activity (such as the ARU fragment of Toxin A, or a derivative thereof (see below)), or a *C. difficile* toxoid as an adjuvant. The following description focuses on *C. difficile* Toxin A, *C. difficile* Toxin B, and *C. difficile* toxoids as specific examples of adjuvants included in the invention. Also included, and subject to the following description, are the toxins and toxoids from other Clostridia, e.g., *C. novyi* (e.g., *C. novyi* α-toxin; Bette et al., Toxicon 29(7):877–887, 1991) and *C. sordellii* (e.g., *C. sordellii* lethal toxin; Bette et al., supra).

Toxin polypeptides for use in the methods and compositions of the invention may be prepared using any of several standard methods. For example, the toxins (e.g., *C. difficile* Toxin A and/or *C. difficile* Toxin B) may be purified from bacterial culture filtrates. (See, e.g., Lyerly et al., FEMS Microbio. Lett. 33:31–35, 1986; and Kim et al., Infection and Immunity 55:2984–2992, 1987; for methods of preparing toxins from *C. difficile* culture filtrates). Toxin polypeptides may also be produced using standard recombinant DNA methods. In these methods, a suitable host cell is transformed with an appropriate expression vector containing all or part of a toxin-encoding nucleic acid fragment. (See Dove et al., Infection and Immunity 58:480–488, 1990, and Barroso et al., Nucleic Acids Research 18:4004, 1990, for the nucleotide and deduced amino acid sequences of *C. difficile* Toxin A, and the nucleotide sequence of Toxin B, respectively). Any of a wide variety of expression systems may be used to produce the recombinant toxins. The toxin polypeptides may be produced in a prokaryotic host (e.g., a bacterium, such as *E. coli*) or in a eukaryotic host (e.g., yeast cells, such as *S. cerevisiae*, mammalian cells (e.g., COS1, NIH3T3, or JEG3 cells), or arthropod cells (e.g., *Spodoptera frugiperda* (SF9) cells)). Such cells are available from a wide range of sources, e.g., the American Type Culture Collection (ATCC), Rockland, Md. (also see, e.g., Ausubel et al., supra). The method of transfection and the choice of expression vector will depend on the host system selected. Transformation and transfection methods are described by, e.g., Ausubel et al., supra. Expression vectors (e.g., plasmid and viral vectors) may be chosen from, e.g., those described in *Cloning Vectors: A Laboratory Manual* (Pouwels et al., 1985, Supp. 1987). Toxin polypeptides, particularly short fragments, may also be produced by chemical synthesis, e.g., by the methods described in *Solid Phase Peptide Synthesis*, 1984, 2nd ed., Stewart and Young, Eds., Pierce Chemical Co., Rockford, Ill., or by standard in vitro translation methods.

Toxoids (e.g., *C. difficile* toxoids) may also be used in the methods and compositions of the invention. A toxoid is a toxin that has been treated so that the toxicity of the toxin is eliminated or reduced, but the adjuvant activity is maintained. Toxoids are prepared using standard methods, for example, by chemical (e.g., glutaraldehyde or formaldehyde) treatment (see, e.g., Libby et al., Infection and Immunity 36:822–829, 1982). Toxoids may also be prepared using standard recombinant DNA methods. For example, mutations can be made in the genes encoding the toxins, and the mutant toxins encoded by the mutant genes can be produced in an expression system, as is described above. Regions in *C. difficile* Toxin A and/or *C. difficile* Toxin B that may be mutated include, e.g., the conserved cysteine residues, the nucleotide binding region, the internal hydrophobic region, and/or the carboxyl-terminal repeat regions. Specific examples of such mutations in *C. difficile* toxins which may be used in the invention are described by, e.g., Barroso et al., Microbial Pathogenesis 16:297–303, 1994.

Other methods of producing toxoids that may be used in the invention include chemical modification of amino acids which are critical for toxicity, but not related to adjuvancy. For example, reagents which specifically modify lysine, tyrosine, tryptophan, histidine, or SH-containing amino acids may be used in the invention, and are known in the art (see, e.g., Cohen et al., Ann. Rev. Biochem. 37:683–695, 1968). In addition, standard photoaffinity labeling methods which employ, e.g., azido-linked substrate derivatives, which are covalently linked to toxin active sites by ultraviolet irradiation, may be used to produce toxoids used in the invention. Also included in the invention is the use of mixtures of toxins and toxoids as adjuvants. For example, a *C. difficile* toxoid may be administered with a trace amount of Toxin A or Toxin B (see, e.g., Tamura et al., Vaccine 12(12):1083–1089, 1994).

In addition to native, full length, *C. difficile* toxins, polypeptide fragments of toxins, or toxins (or polypeptide fragments of toxins) containing mutations (which may or may not be toxoids) may be used in the invention, provided that adjuvant activity is retained. For examples of fragments of *C. difficile* toxins, see, e.g., Price et al., Current Microbiology 16:55–60, 1987; Lyerly et al., Current Microbiology 21:29–32, 1990; and Frey et al., Infection and Immunity 60:2488–2492, 1992. Genes encoding fragments of *C. difficile* toxins, and/or toxins containing mutations, are made using standard methods (see, e.g., Ausubel et al., supra). Fragments, derivatives, and toxoids included in the invention may be screened for adjuvant activity using standard methods in the art, e.g., by measuring induction of a mucosal immune response or induction of protective and/or therapeutic immunity (see below). As is described below, the ARU fragment of *C. difficile* Toxin A is an effective mucosal adjuvant.

Fusion proteins containing a Clostridium (e.g., *C. difficile*) toxin (or a fragment or derivative thereof having adjuvant activity) fused to, e.g., an antigen of a pathogen (e.g., *H.* pylori urease), are also included in the invention, and may be prepared using standard methods (see, e.g., Ausubel et al., supra). In addition, the toxin adjuvants of the invention may be covalently coupled or cross-linked to antigens (see, e.g., Cryz et al., Vaccine 13:67–71, 1994; Liang et al., J. Immunology 141:1495–1501, 1988; and Czerkinsky et al., Infection and Immunity 57:1072–1077, 1989).

The adjuvant/vaccine compositions of the invention may be administered to mucosal (e.g., intranasal, oral, ocular, gastrointestinal, rectal, vaginal, or genito-urinary) surfaces. Alternatively, parenteral (e.g., intravenous, subcutaneous, intraperitoneal, or intramuscular) modes of administration may be used. The amounts of adjuvant and vaccine administered depend on the particular vaccine antigen and adjuvant, the mode and frequency of administration, and the desired effect (e.g., protection and/or treatment), as determined by one skilled in the art. In general, the adjuvants of the invention will be administered in amounts ranging between 1 ng and 1 mg, with antigens ranging between 1 µg and 100 mg. Administration is repeated as is determined to be necessary by one skilled in the art. For example, a priming dose may be followed by 3 booster doses at weekly intervals.

The adjuvants of the invention (in combination with an antigen) are administered in a pharmaceutically acceptable carriers or diluents (e.g., water, a saline solution (e.g., phosphate-buffered saline), a bicarbonate solution (e.g., 0.24 M NaHCO$_3$), a suppository, cream, or jelly), which are selected on the basis of the mode and route of administration, and standard pharmaceutical practice. Suitable pharmaceutical carriers and diluents, as well as pharmaceutical necessities for their use in pharmaceutical formulations, are described in *Remington's Pharmaceutical Sciences* (Alfonso Gennaro et al., eds., 17th edn., Mack Publishing Co., Easton Pa., 1985), a standard reference text in this field, in the USP/NF, and by Lachman et al. (*The Theory & Practice of Industrial Pharmacy,* 2nd edn., Lea & Febiger, Philadelphia Pa., 1976). In the case of rectal and vaginal administration, the vaccines are administered using methods and carriers standardly used in administering pharmaceutical materials to these regions. For example, suppositories, creams (e.g., cocoa butter), or jellies, as well as standard vaginal applicators, droppers, syringes, or enemas may be used, as determined to be appropriate by one skilled in the art.

The following examples are meant to illustrate, but not to limit, the methods and compositions of the invention. Modifications of the conditions and parameters set forth below that are apparent to one skilled in the art are included in the invention.

EXAMPLES

Example I

Adjuvant Activity of *C. difficile* Toxins Administered with Ovalbumin (OVA) or Keyhole Limpet Hemocyanin (KLH)

In order to analyze the adjuvant activity of *C. difficile* Toxin A, female Swiss Webster Mice (Taconic Farms, Germantown, N.Y.) were intranasally immunized with an antigen (50 μg of either ovalbumin (OVA) or Keyhole Limpet Hemocyanin (KLH)) either alone or in combination with Toxin A (40 ng). As a control, the vaccine antigens were administered with *E. coli* heat-labile toxin (LT; 5 μg), which is known to have mucosal adjuvant activity. The immunization regimen involved administration once per week for four consecutive weeks. Samples were taken from the animals one week after the final immunization.

Intranasal immunization of OVA with Toxin A or LT resulted in significantly higher induction of OVA-specific IgA antibody responses in serum, salivary, fecal, and vaginal samples, compared to similar samples from animals which were administered OVA without an adjuvant (FIG. 1A). OVA-specific IgG levels in serum were generally higher than the levels of OVA-specific IgA in serum and mucosal samples, even without the addition of adjuvant, but were enhanced in the presence of adjuvant (FIG. 1A). OVA-specific mucosal IgA was only significantly detectable in animals which were administered an adjuvant with the antigen (FIG. 1A).

Similarly, KLH-specific mucosal immune responses (IgG and IgA) were elevated in mice administered intranasally with KLH+Toxin A or LT, compared to mice administered KLH without adjuvant (FIG. 1B).

A statistical comparison of immune responses to antigens (OVA and KLH) generated in the presence versus the absence of adjuvant treatment is summarized in Table 1, below.

TABLE 1

Wilcoxon ranked sums analysis for OVA and KLH administered with Toxin A: Immune responses compared by treatment groups. No statistically differences were detected between OVA/KLH + Toxin A and OVA/KLH + LT treatment groups.

| | | | | |
|---|---|---|---|---|
| Ranked sums p values (OVA) | | | | |
| OVA + Toxin A (40 ng) treatment compared to OVA alone | | | | |
| | serum IgA | salivary IgA | fecal IgA | vaginal IgA |
| p value | 0.1172 | 0.009 | 0.009 | 0.009 |
| | serum IgG | salivary IgG | fecal IgG | vaginal IgG |
| p value | 0.0758 | 0.1172 | 0.009 | 0.0163 |
| OVA + LT (5 μg) treatment compared to OVA alone | | | | |
| | serum IgA | salivary IgA | fecal IgA | vaginal IgA |
| p value | 0.1172 | 0.1172 | 0.0283 | 0.0361 |
| | serum IgG | salivary IgG | fecal IgG | vaginal IgG |
| p value | 0.1172 | 0.009 | 0.009 | 0.758 |
| Ranked sums p values (KLH) | | | | |
| KLH + Toxin A (40 ng) treatment compared to KLR alone | | | | |
| | serum IgA | salivary IgA | fecal IgA | vaginal IgA |
| p value | 0.0283 | 0.009 | 0.1425 | 0.009 |
| | serum IgG | salivary IgG | fecal IgG | vaginal IgG |
| p value | 0.3472 | 0.009 | 0.0163 | 0.0283 |
| KLH + LT (5 μg) treatment compared to KLH alone | | | | |
| | serum IgA | salivary IgA | fecal IgA | vaginal IgA |
| p value | 0.6015 | 0.009 | 0.009 | 0.016 |
| | serum IgG | salivary IgG | fecal IgG | vaginal IgG |
| p value | 0.6015 | 0.009 | 0.009 | 0.009 |

Methods

Antigen and Adjuvant Preparation

Ovalbumin (OVA; Turkey, Sigma Chemical Co., St. Louis, Mo.) or Keyhole Limpet Hemocyanin (KLH; Southern Biotech., Birmingham, Ala.) was diluted in phosphate buffered saline (PBS) to final concentration of 5 mg/ml. Recombinant urease (rUrease) was prepared from recombinant *E. coli* by lysis, ultrafiltration, DEAE sepharose chromatography, and Q-sepharose chromatography (Lee et al., J. Infect. Dis. 172:161–172, 1995). Lyophilized purified urease was reconstituted in PBS to a concentration of 4 mg/ml. Lyophilized *E. Coli* heat-labile enterotoxin (LT; Berna, Coral Gables, Fla.) and was reconstituted in PBS to a concentration of 1 mg/ml.

Toxin A was purified from *C. difficile* culture filtrates by ammonium sulfate precipitation, DEAE chromatography, and acid precipitation. Toxin B was purified from *C. difficile* culture filtrates by DEAE chromatography (Lyerly et al., supra, 1986).

ELISA Analysis of the Immune Responses

The immune responses of immunized mice were measured by ELISA analysis of serum (IgG and IgA), salivary (IgA), fecal (IgA), and vaginal (for IgA) samples for antibodies against the appropriate antigen (OVA or KLH). Serum samples were obtained by retro-orbital bleeding under isoflurane anesthesia. Saliva samples were obtained after pilocarpine treatment (100 mg/kg). To obtain vaginal samples, wicks pre-wetted with protease inhibitors (200 $\mu$M amino ethyl benzene sulfonyl fluoride (AEBSF), 0.1% Aprotinin, 0.01 $\mu$M Leupeptin, and 3.25 $\mu$M Bestatin) were placed in the animals. Feces and wicks containing vaginal samples were resuspended in the protease inhibitor solution in 2.5% non-fat dry skim milk prior to analysis.

Figure 1A:
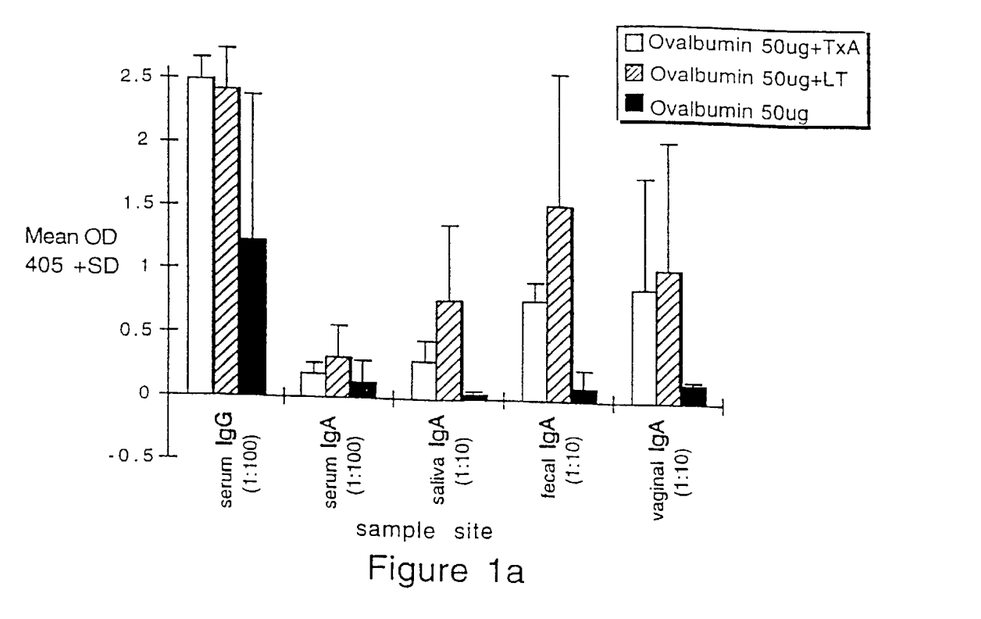
Figure 1B:
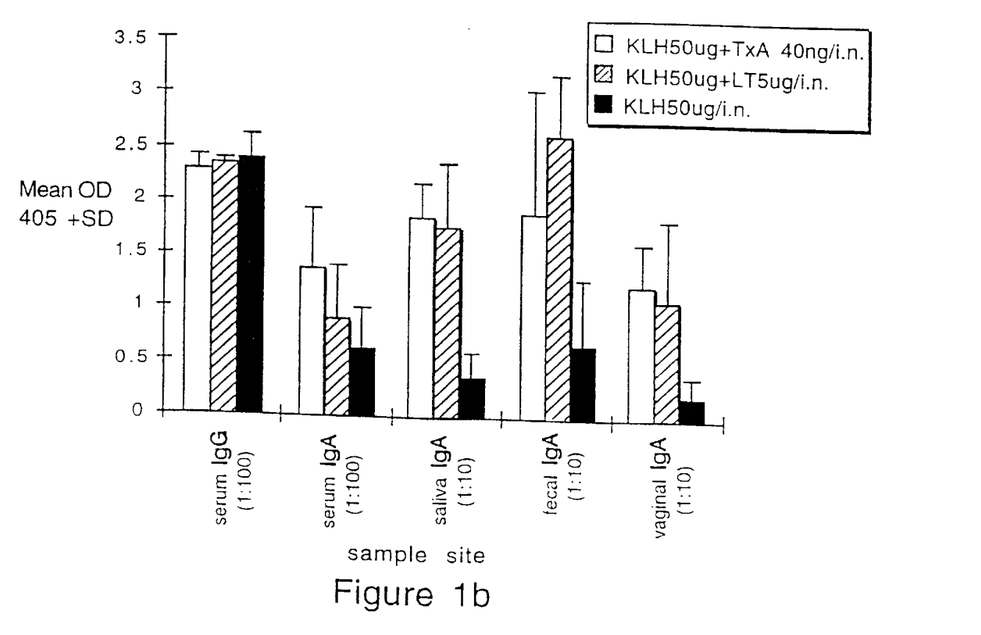

For ELISA analysis, the wells of 96-well plates, coated in carbonate coating buffer (0.1 M carbonate, pH 9.6), were incubated with antigen at a concentration of 10 $\mu$g/ml overnight at 4° C., followed by blocking for 1 hour at 37° C. with 2.5% non-fat dry skim milk in PBS with 2% Tween 20 (Sigma Chemical Co., St. Louis, Mo.). Serum antibodies were assayed at a dilution of 1:100 in blocking solution, and mucosal samples were assayed at a 1:10 dilution. Specific IgG antibodies were detected using a goat anti-mouse IgG alkaline phosphatase conjugate, and specific IgA antibodies were measured with a goat anti-mouse IgG alkaline phosphatase conjugate. The results are presented in FIGS. 1A and 1B as mean $OD_{405}$ readings from each treatment group.

Example II

Adjuvant Activity of *C. difficile* Toxins with *H. pylori* Urease

The following experiments show that mucosal immune responses to *H. pylori* urease are enhanced when the antigen is administered intranasally with a low, non-toxic dose of *C. difficile* Toxin A or *C. difficile* Toxin B, and further that this immune response is protective against subsequent Helicobacter challenge.

*H. pylori* urease apoenzyme (5 $\mu$g) purified from recombinant *E. coli* expressing the urease structural subunits (Lee et al., supra) was administered intranasally to female Swiss Webster mice (5 mice/adjuvant) once per week for four consecutive weeks in combination with *C. difficile* Toxin A (0.2 $\mu$g), *C. difficile* Toxin B (1 $\mu$g), *C. difficile* Toxoid culture filtrate (containing 15 $\mu$g each Toxin A and Toxin B inactivated with 1% formalin), CT (5 $\mu$g), the B subunit of CT (CTB; 5 $\mu$g)+CT (10 ng), or without adjuvant. The adjuvancy of the toxins was determined by: (1) measuring the induction of urease-specific mucosal IgA, and (2) observing the induction of protective immunity.

Induction of Mucosal IgA

One week after the final urease immunization, fecal, salivary, and vaginal samples were obtained from the mice for analysis of the anti-urease IgA mucosal immune response. Fecal samples were prepared by homogenizing several fecal pellets in protease inhibitor solution (200 $\mu$M AEBSF, 0.1% Aprotinin, 0.01 $\mu$M Leupeptin, 3.25 $\mu$M Bestatin); salivary samples were obtained by pilocarpine induction under ketamine anesthetic; and vaginal samples were obtained by inserting absorbent wicks, pre-wetted with protease inhibitor solution (see above), into animals under isoflurane anesthesia.

Figure 2:
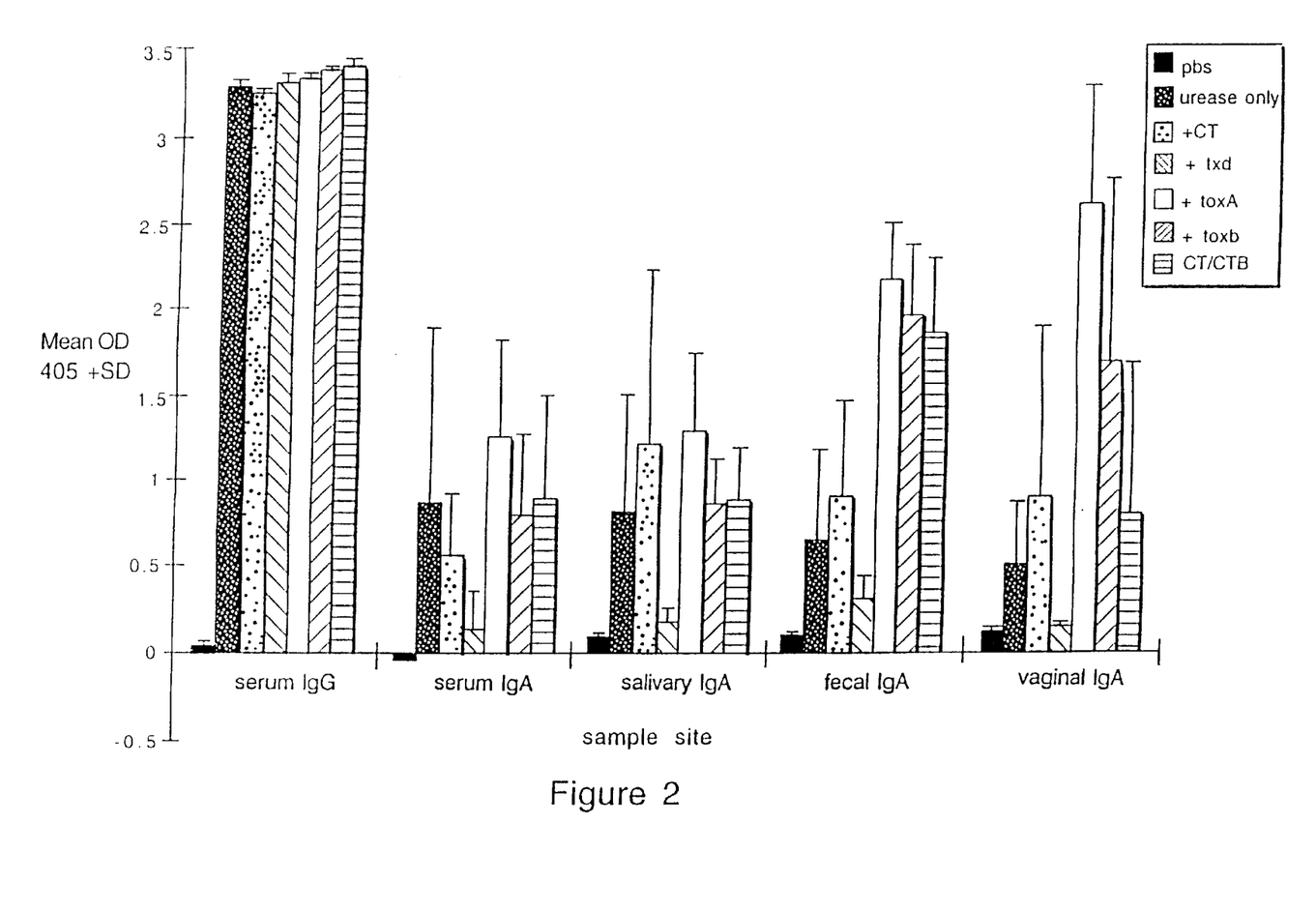
FIG. 2 is a series of graphs showing the levels of urease-specific IgG in serum and urease-specific IgA in serum, saliva, feces, and vaginal secretions obtained from mice immunized intranasally with urease (5 μg) and the indicated adjuvants (PBS=phosphate buffered saline (no adjuvant); urease only (no adjuvant);+CT=urease+5 μg CT (cholera toxin);+txd=urease+15 μg txd (toxoid);+toxA= urease+0.2 μg toxA (*C. difficile* Toxin A);+toxb=urease+1 μg toxB (*C. difficile* Toxin B); CT/CTB=urease+5 ng CT (cholera toxin) and 5 μg CTB (cholera toxin B subunit)). The mean duplicate reading ($OD_{405}$) using single dilutions (serum, 1:100; mucosal samples, 1:20) of primary antibody is shown in the graphs. The antibody levels shown represent the mean of 5 animals in each group.

Anti-urease IgA levels in the samples were measured by ELISA. The wells of a 96-well plate were coated with urease (0.5 $\mu$g/well) in carbonate coating buffer (see above), blocked with 2.5% non-fat dry skim milk, and contacted with the mouse samples. The level of anti-urease IgA was determined by applying a goat anti-mouse IgA antibody labeled with alkaline phosphatase to the wells and measuring the absorbance at 405 nanometers visible light (FIG. 2).

Antibody levels in each treatment group were compared by the Wilcoxon Ranked Sums test (Table 2). Serum anti-urease IgG levels were enhanced in all groups to which urease was administered intranasally, and did not differ significantly in the various treatment groups. Fecal anti-urease IgA levels were significantly enhanced when Toxin A or Toxin B was co-administered with urease, as compared to the levels induced by administration of urease alone, or urease with CT. There was no difference in fecal anti-urease IgA in animals administered urease with Toxin A or B compared to animals administered urease with a combination of CTB and CT. Vaginal IgA levels against urease were significantly higher when Toxin A was co-administered with urease, compared with the other treatment groups. This difference was statistically significant when compared to urease administered alone or with any other adjuvant combination tested.

TABLE 2

Statistical analysis of mucosal responses to urease by adjuvant treatment. Differences in antibody responses in feces, saliva, and vaginal secretions are shown between groups administered urease alone, urease with CT, or urease with CTB + CT; and groups administered urease with Toxin A, urease with Toxin B, or urease with toxoid (Wilcoxon ranked sums).

| treatment: | CT | CTB + CT | urease only |
|---|---|---|---|
| Fecal IgA: | | | |
| Toxin A | 0.0119 | 0.1172 | 0.009 |
| Toxin B | 0.0163 | 0.9166 | 0.0163 |
| toxoid | not done | not done | 0.4647 |
| Salivary IgA: | | | |
| Toxin A | 0.8345 | 0.2101 | 0.2087 |
| Toxin B | 0.6752 | 0.9168 | 0.4647 |
| toxoid | not done | not done | 0.0749 |
| Vaginal IgA: | | | |
| Toxin A | 0.0283 | 0.0283 | 0.009 |
| Toxin B | 0.1745 | 0.1172 | 0.0937 |
| toxoid | not done | not done | 0.0472 |

Thus, *C. difficile* Toxin A and *C. difficile* Toxin B significantly enhance mucosal immune responses to a heterologous antigen in multiple compartments when administered intranasally. In particular, strong genito-urinary and intestinal tract responses are induced when Toxin A is administered to the upper respiratory tract. This enhancement is stronger than that observed with other known mucosal adjuvants; other adjuvants (e.g., CT, LT, and CT+CT B) stimulate principally respiratory tract immunity when administered intranasally with antigens.

Induction of Protective Immunity

To determine whether the immune responses induced by *C. difficile* toxins were associated with protection against challenge, immunized animals were challenged with *H. felis*. *H. felis* ($1 \times 10^7$) was administered intragastrically to anesthetized female Swiss Webster mice 14 days after the final immunization with urease. Animals were sacrificed 14 days later, and gastric biopsies (antrum) were analyzed for urease activity to determine the presence of *H. felis*. Biopsy samples were incubated in Rapid Urease Broth (buffered urea solution with phenol red pH indicator) for 4 hours. Stomach material was removed by centrifugation and the $OD_{550}$ was measured. The density of bacterial colonization is reflected by the $OD_{550}$ measurement (quantity of gastric urease activity) and correlates with bacterial density observed by histopathology. Mice with absorbance readings of higher than 2× background were considered to be infected. Partial protection is defined as $OD_{550}$ levels higher than background and less than 2× the SD of infected controls (PBS group).

Figure 3:
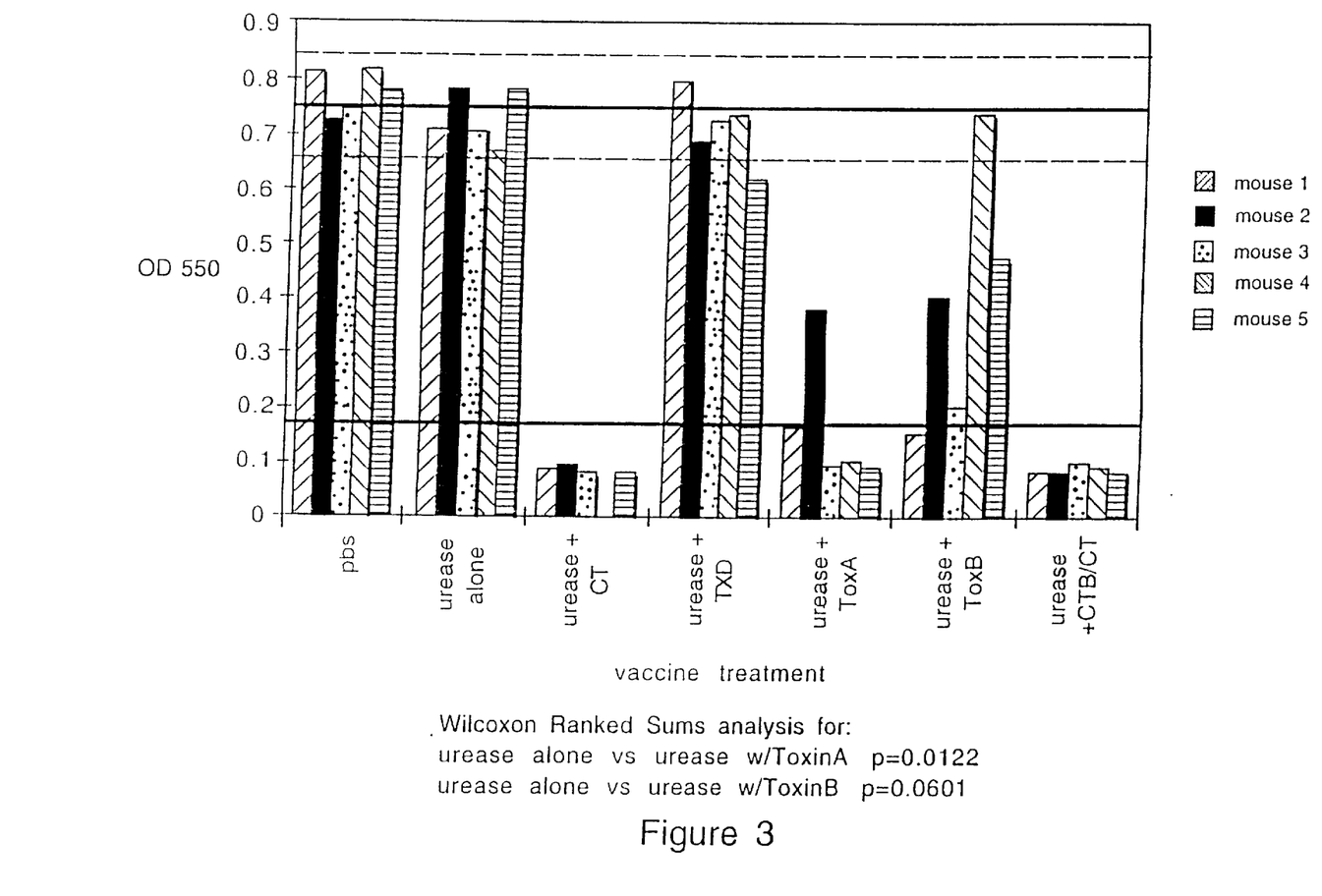
FIG. 3 is a graph showing the urease activity in gastric tissue of mice immunized intranasally with urease (5 μg) in combination with the indicated adjuvants, and subsequently challenged with virulent *Helicobacter felis* (see above description of FIG. 2). Gastric tissue samples were taken 2 weeks after *H. felis* challenge.
Figure 4A:
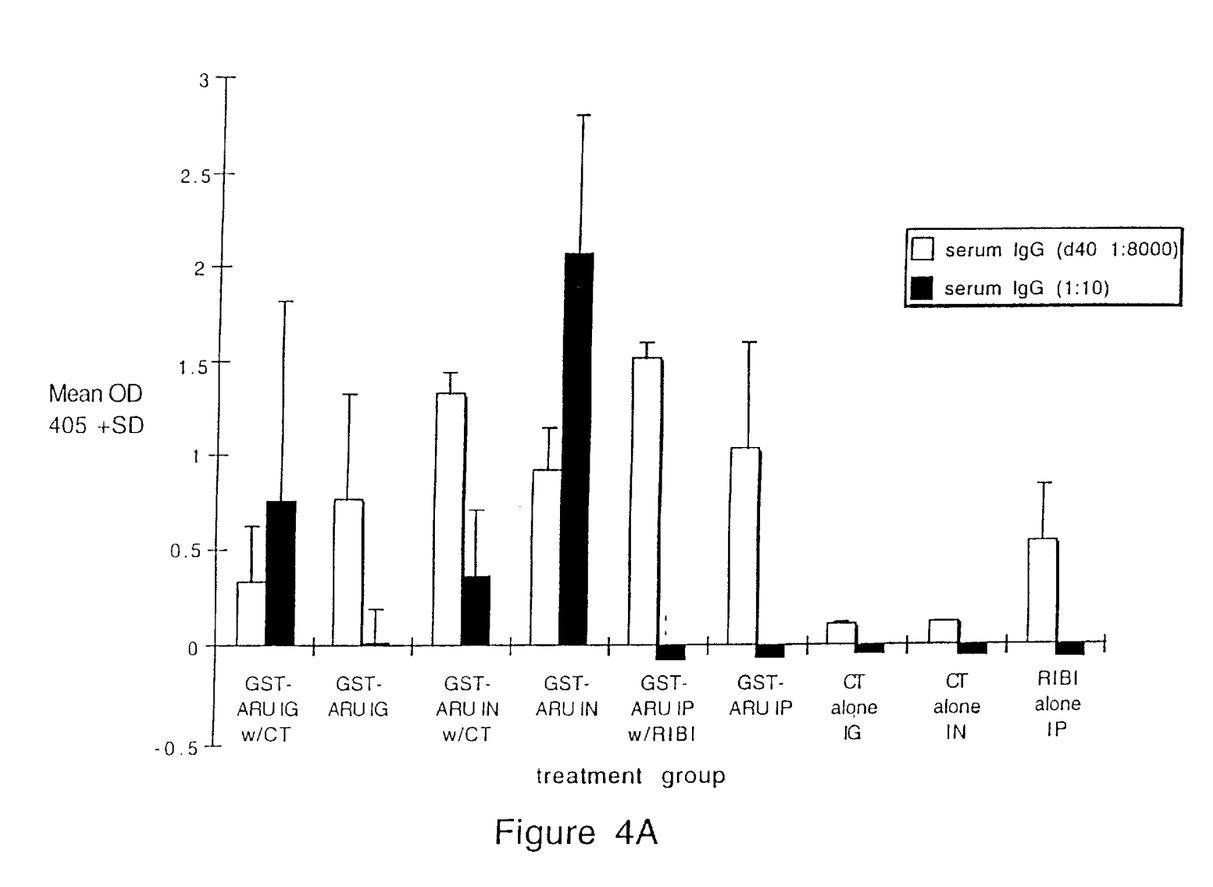
FIGS. 4A–4B are graphs showing the levels of anti-*C. difficile* Toxin A IgG and IgA in serum (FIG. 4A) and salivary, fecal, and vaginal samples (FIG. 4B), as measured by ELISA, from mice immunized with fusion proteins containing the carboxyl-terminal region of Toxin A (GST-ARU), according to the scheme illustrated in Table 4.
Figure 4B:
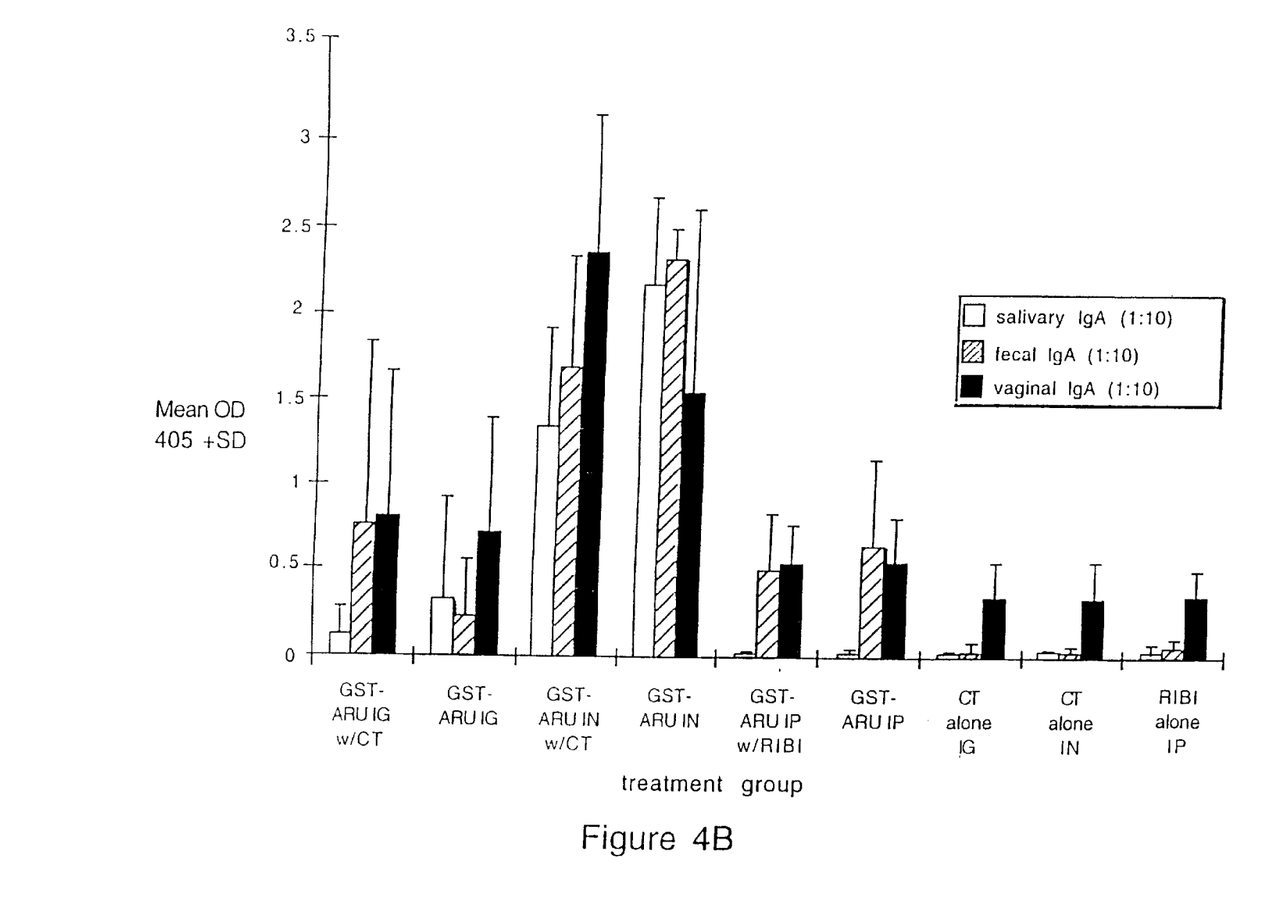

FIG. 3 shows the results of the gastric urease assay, and the protection results are summarized in Table 3. Urease alone and urease administered with *C. difficile* toxoid were ineffective in inducing protective immunity in challenged animals. Urease administered with CT or CT+CTB completely protected 4/4 and 5/5 animals, respectively, while urease administered with Toxin A completely protected 3/5 animals and partially protected 5/5. Wilcoxon ranked sums analysis showed that the magnitude of infection, as determined by measuring the $OD_{550}$, was significantly lower in the animals administered urease+Toxin A, compared with those administered urease alone (p=0.0122). Animals immunized with urease+Toxin B also had lower grade infections than those immunized with urease alone, and 4/5 animals immunized with urease+Toxin B were partially protected. These data show that *C. difficile* Toxin A and Toxin B, when administered intranasally with *H. pylori* urease, induce protective immunity to *H. felis* challenge.

TABLE 3

Protection of mice from *H. felis* colonization after intranasal immunization with urease and mucosal adjuvants.

| Treatment | infected mice/total |
| --- | --- |
| PBS | 5/5 |
| urease alone | 5/5 |
| urease + CT | 0/4 |
| urease + toxoid | 5/5 |
| urease + Toxin A | 1/5* |
| urease + Toxin B | 4/5** |
| urease + CTB + CT | 0/5 |

*1 infected animal was less heavily colonized than controls
**3 infected animals were less heavily colonized than controls Example III Synthesis of a *C. difficile* Toxin A Fusion Protein (GST-ARU)

The carboxyl-terminal region of *C. difficile* Toxin A contains a series of repeating amino acid units and is thought to be involved in binding of the toxin to carbohydrate residues on target cells (see, e.g., Lyerly et al., Current Microbiology 21:29–32, 1990; Frey et al., Infection and Immunity 60:2488–2492, 1992; and references cited therein). A fusion protein consisting of the carboxyl-terminal region of *C. difficile* Toxin A fused to glutathione S-transferase (GST) was constructed, as follows. Using standard methods, a Sau3A fragment containing nucleotides which encode the 794 carboxyl-terminal amino acids of Toxin A was isolated (see, e.g., Dove et al., supra, for the sequence of the Toxin A gene). The sticky ends of the fragment were filled in, and the blunt-ended fragment was ligated into SmaI-digested pGEX3X (Pharmacia, Piscataway, N.J.). Clones containing a plasmid encoding GST-ARU were grown in *Escherichia coli*, and the GST-ARU fusion protein was purified on a glutathione-agarose affinity column, eluted from the column by free glutathione, and dialyzed to remove the glutathione, using standard methods. GST-ARU is non-toxic.

Example IV

Adjuvant Activity of a *C. difficile* Toxin A Fusion Protein (GST-ARU)

A. Administration of GST-ARU Induces an Anti-Toxin A Immune Response

GST-ARU was expressed in *E. coli*, affinity-purified, using standard methods, and administered to mice in the experiments illustrated in Table 4.

TABLE 4

Experimental scheme for analysis of the mucosal immune response after immunization of mice with a fusion protein containing the carboxyl terminus of *C. difficile* Toxin A. GST-ARU = fusion protein containing glutathione S-transferase and Toxin A Repeating Units; GST = glutathione S-transferase; PBS = phosphate buffered saline; IG = intragastric; IN = intranasal; IP = intraperitoneal. Immunizations were carried out on days 0, 7, 14, and 21. Serum, vaginal, fecal, and salivary samples were taken on day 28.

| Antigen | Dose (μg) | Adjuvant | Route | # Mice |
|---|---|---|---|---|
| GST-ARU | 100 | CT | IG | 5 |
| GST-ARU | 100 | none | IG | 5 |
| GST-ARU | 50 | CT | IN | 5 |
| GST-ARU | 50 | none | IN | 5 |
| GST-ARU | 25 | RIBI | IP | 5 |
| GST-ARU | 25 | none | IP | 5 |
| GST | 25 | CT | IG | 5 |
| GST | 25 | none | IG | 5 |
| GST | 12.5 | CT | IN | 5 |
| GST | 12.5 | none | IN | 5 |
| GST | 6.25 | RIBI | IP | 5 |
| GST | 6.25 | none | IP | 5 |
| PBS | 0 | CT | IG | 5 |
| PBS | 0 | CT | IN | 5 |
| PBS | 0 | RIBI | IP | 5 |

Anti-*C. difficile* Toxin A IgA and/or IgG levels in the samples were measured by ELISA. The wells of a 96-well plate were coated with Toxin A (1 μg/well) in carbonate coating buffer (see above), blocked with 2.5% non-fat dry skim milk, and contacted with the samples. The level of anti-urease IgA (or IgG) was determined by applying a goat anti-mouse IgA (or IgG) antibody labeled with alkaline phosphatase to the wells and measuring the absorbance at 405 nanometers visible light.

The results of these experiments are shown in FIGS. 4A–4B. These data show that CT is not required for enhanced induction of anti-Toxin A serum IgA or IgG, or anti-Toxin A mucosal immune responses. This effect is particularly apparent after intranasal immunization (FIGS. 4A–4B). Because the carboxyl-terminal region of Toxin A is capable of inducing immune responses without a heterologous adjuvant (i.e., CT), these data indicated that this region of Toxin A may be useful as an adjuvant. However, GST alone (i.e., GST which is not in the form of a fusion protein with ARU) was not found to be antigenic when administered mucosally or systemically, in the presence or absence of known adjuvant. Thus, GST is not a suitable test antigen for *C. difficile* toxin-antigen fusion proteins. In the experiments described below, GST-ARU was shown to be an effective adjuvant when administered intranasally with ovalbumin.

B. Intranasal Administration of GST-ARU+Ovalbumin Leads to an Anti-Ovalbumin Immune Responses The adjuvant activity of GST-ARU was tested by intranasal immunization of GST-ARU and/or Toxin A with ovalbumin. Mice were intranasally administered 100 μg ovalbumin, 25 μg GST-ARU, and decreasing amounts of Toxin A (200 ng, 40 ng, 8 ng, 1.6 ng, and 0 ng), or 100 μg ovalbumin and decreasing amounts of Toxin A (200 ng, 40 ng, 8 ng, 1.6 ng, and 0 ng), but no GST-ARU, at four weekly intervals. The volume administered did not exceed 20 μL, and was administered without anesthesia. Five mice were in each treatment group.

Figure 5A:
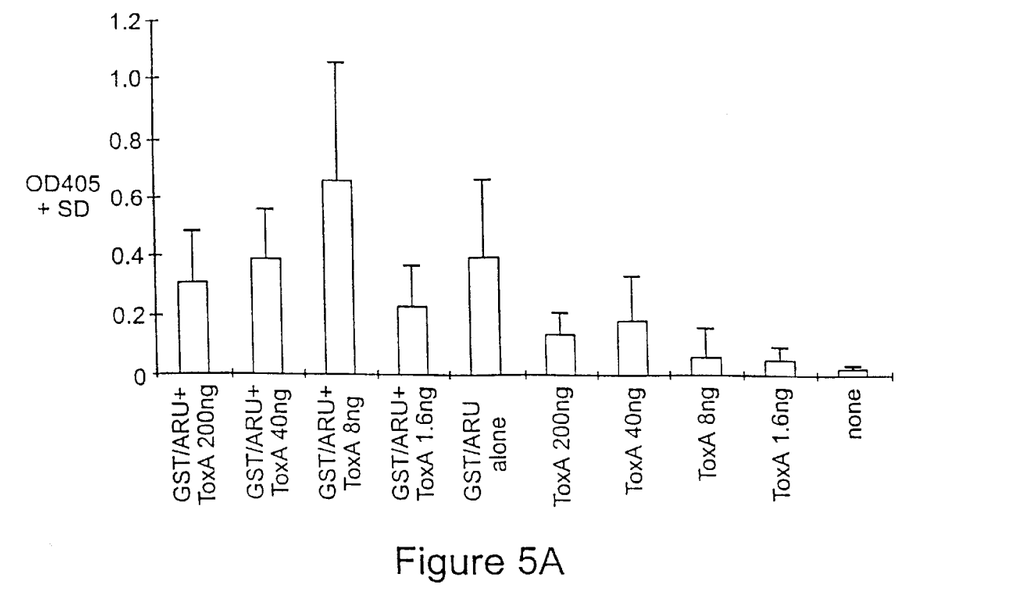
FIGS. 5A–5B are graphs showing the levels of anti-ovalbumin serum IgA (FIG. 5A) and serum IgG (FIG. 5B) in mice immunized intranasally with ovalbumin+GST/ARU and/or Toxin A, as indicated. The bars indicate the mean antibody levels in each group of 5 mice. Standard deviations (SD) are indicated.
Figure 5B:
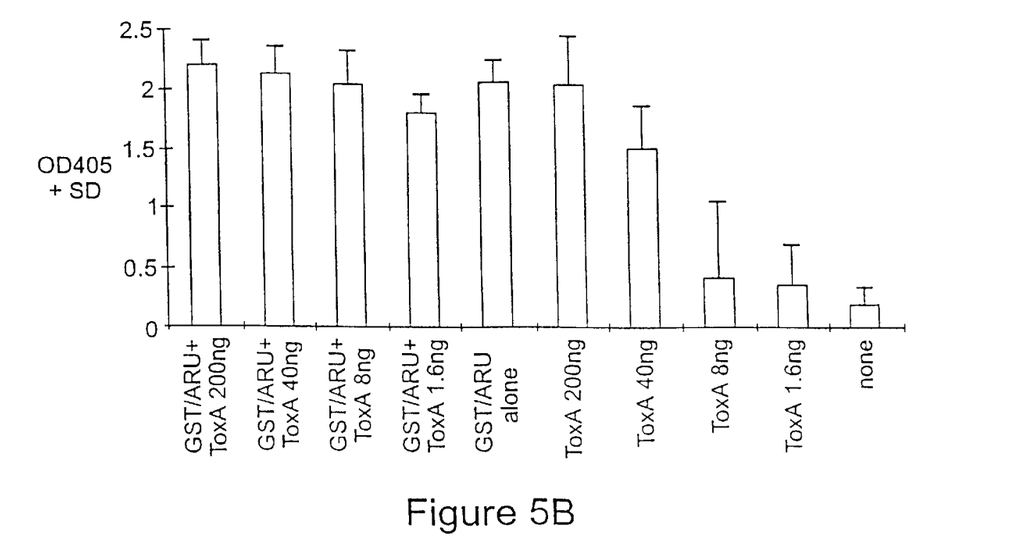
Figure 6A:
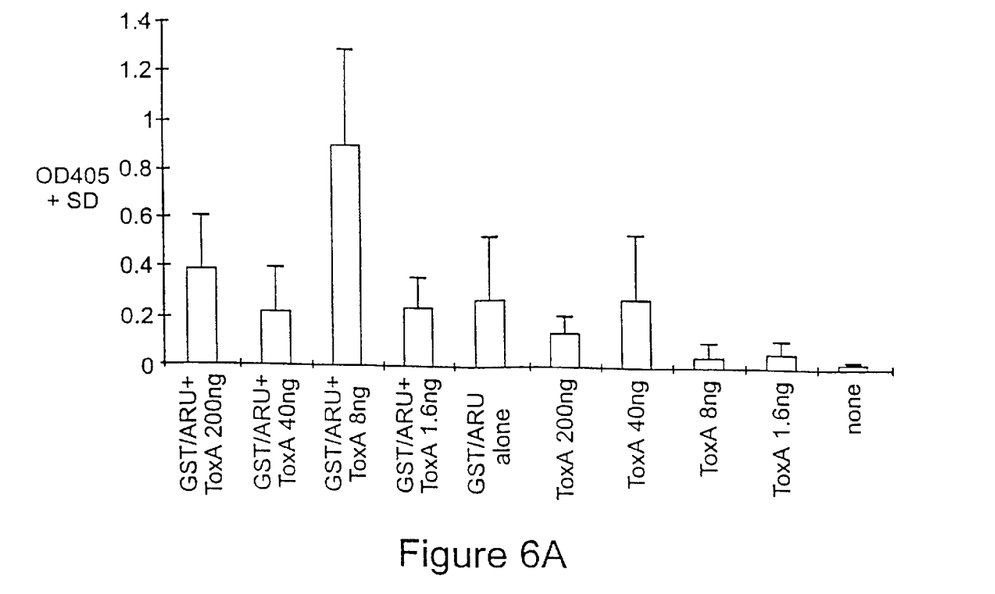
FIGS. 6A–6B are graphs showing the levels of anti-ovalbumin salivary IgA (FIG. 6A) and fecal IgA (FIG. 6B) in mice immunized intranasally with ovalbumin+GST/ARU and/or Toxin A, as indicated. The bars indicate the mean antibody levels in each group of 5 mice. Standard deviations (SD) are indicated.
Figure 6B:
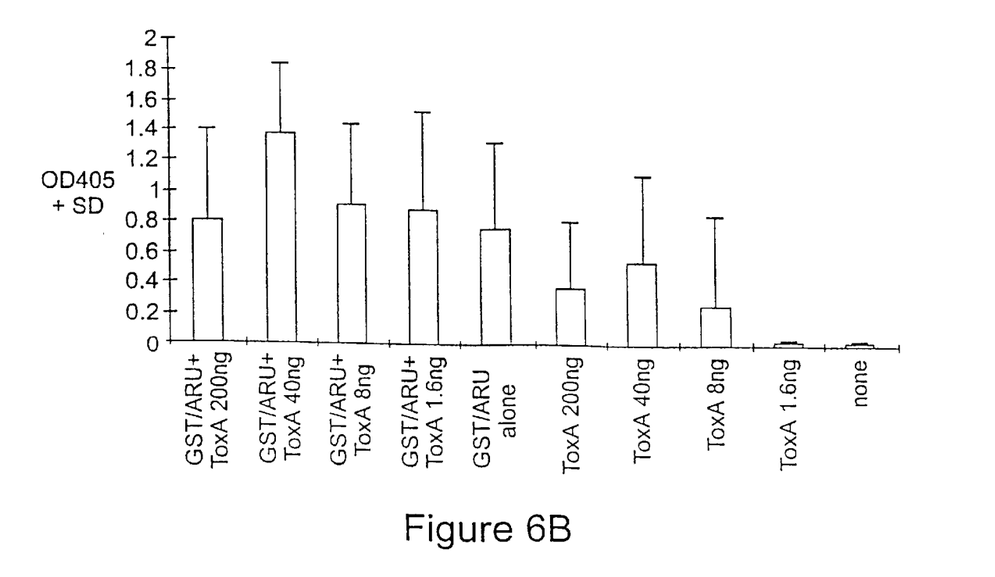
Figure 7A:
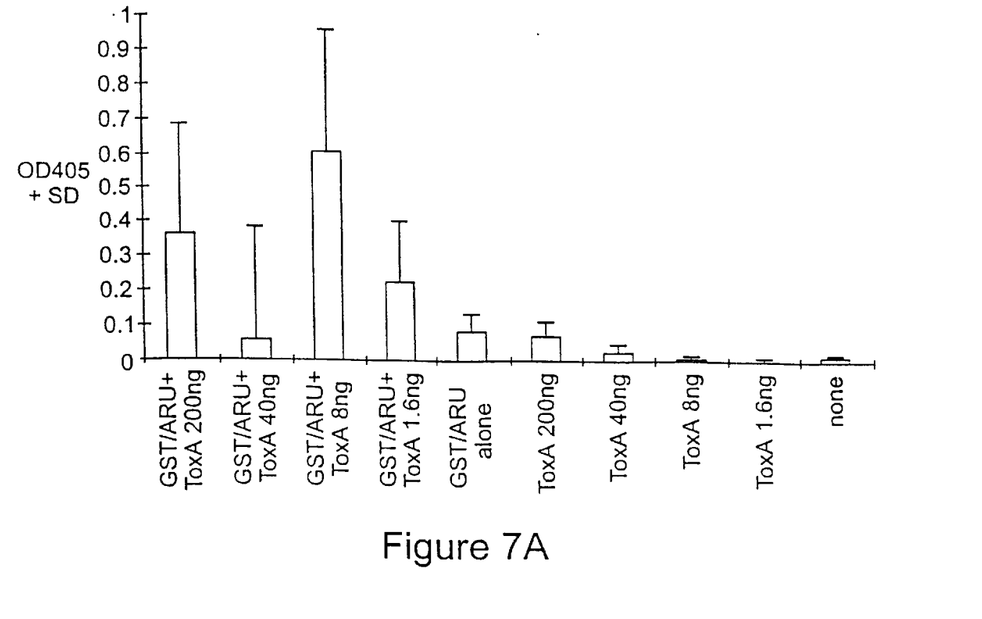
FIGS. 7A–7B are graphs showing the levels of anti-ovalbumin vaginal IgA (FIG. 7A) and vaginal IgG (FIG. 7B) in mice immunized intranasally with ovalbumin+GST/ARU and/or Toxin A, as indicated. The bars indicate the mean antibody levels in each group of 5 mice. Standard deviations (SD) are indicated.
Figure 7B:
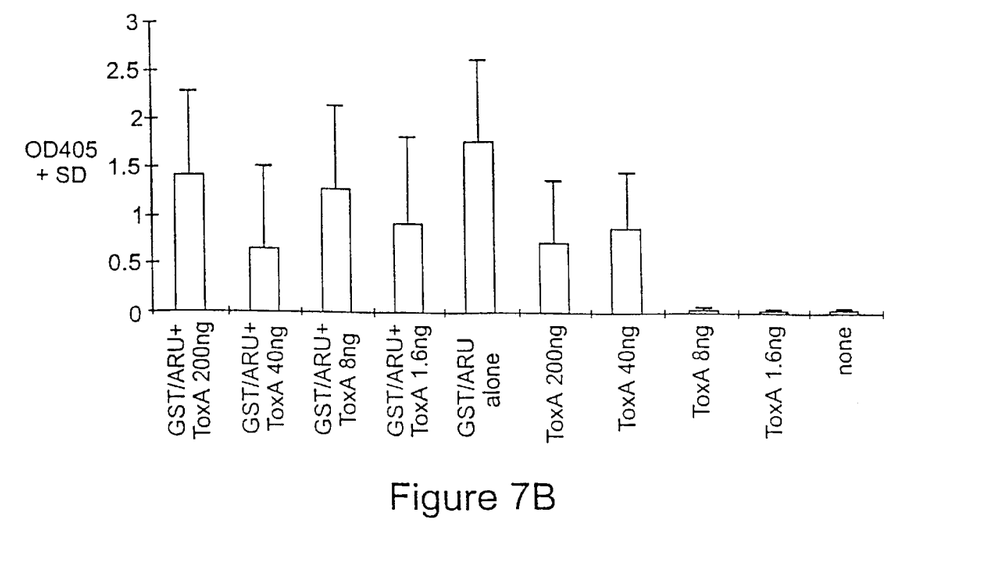
Figure 8:
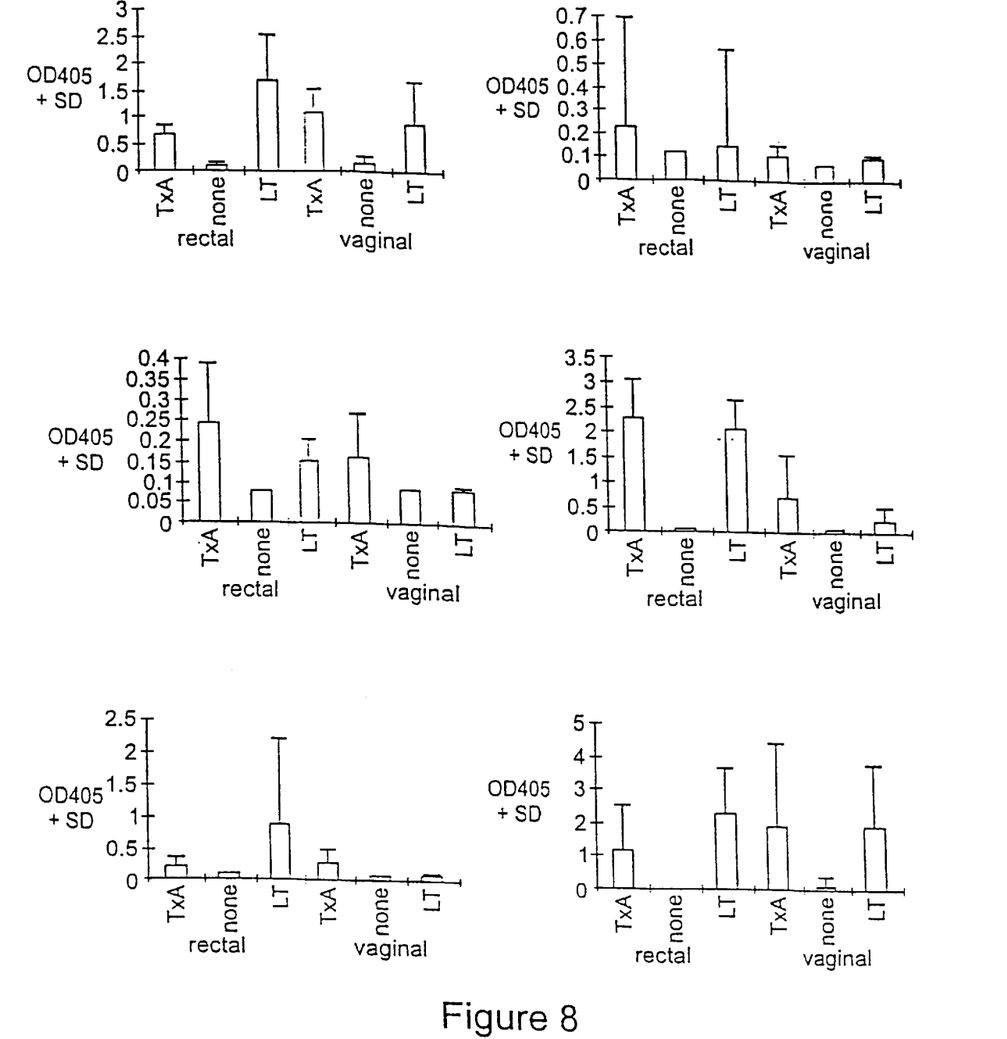
FIG. 8 is a series of graphs showing the levels of anti-ovalbumin serum IgG, serum IgA, salivary IgA, fecal IgA, vaginal IgA, and vaginal IgG in mice immunized rectally (Rec) or vaginally (Vag) with ovalbumin, ovalbumin+Toxin A, or ovalbumin+LT, as indicated. The bars indicate the mean antibody levels in each group of 5 mice. Standard deviations (SD) are indicated.

The anti-ovalbumin immune responses in serum, saliva, feces, and vaginal secretions were determined by ELISA analysis, as is described above (see FIGS. 5A–7B). The serum IgA and IgG responses show decreasing levels of anti-ovalbumin antibodies in animals given decreasing doses of Toxin A alone. The responses did not diminish when GST-ARU was given with the decreasing doses of active toxin, even when no Toxin A was administered (FIGS. 5A and 5B). Similarly, the salivary, fecal, and vaginal anti-ovalbumin IgA levels were enhanced when GST-ARU was used as an adjuvant, regardless of the presence of active Toxin A (FIGS. 6A–7B). All immune responses analyzed were significantly enhanced when GST-ARU was used as an adjuvant, compared to ovalbumin administered alone. These responses did not differ significantly in magnitude from the responses observed using LT as an adjuvant (Table 5). Thus, antibody levels by ELISA, as is described above. Serum anti-ovalbumin IgG immune responses were enhanced when the antigen was administered with Toxin A by the rectal or vaginal route, but not when the antigen was administered alone (FIG. 8). The anti-ovalbumin IgA antibody response was greatly elevated in feces, and slightly enhanced in serum, saliva, and vaginal secretions, when Toxin A was used as an adjuvant (FIG. 8). All immune responses measured after rectal immunization of ovalbumin+adjuvant were statistically greater than those measured after rectal immunization of ovalbumin alone (Table 6). A similar trend is apparent with vaginal immunizations, but larger numbers of mice are required to demonstrate statistical significance. Interestingly, the vaginal anti-ovalbumin IgG response was elevated when ovalbumin was administered rectally or vaginally with adjuvants, as compared to when the antigen was administered alone. These data show that Toxin A increases specific antibody levels in serum and mucosal secretions when administered to the rectal or vaginal mucosa. As further support for the efficacy of the rectal route, using challenge and assay methods similar to those described above, mice rectally immunized with Helicobacter urease and Toxin A were shown to be protected against Helicobacter challenge.

TABLE 6

Wilcoxon ranked sums analysis for rectal immunization of ovalbumin + Toxin A

| treatment | Serum IgG | Serum IgA | Salivary IgA | Salivary IgG | fecal IgA | fecal IgG | vaginal IgA | vaginal IgG |
|---|---|---|---|---|---|---|---|---|
| rectal toxin A v Ovalbumin alone | 0.009 | 0.009 | 0.009 | 0.0278 | 0.0089 | 0.0088 | 0.0088 | 0.0088 |
| rectal toxin A v rectal LT | 0.0864 | 0.6242 | 0.2207 | 1 | 0.6242 | 0.8065 | 0.3272 | 0.3272 |

GST-ARU significantly enhances the immune response to co-administered antigens in serum and mucosal secretions. In addition, these data show that the toxicity of Toxin A can be removed genetically, without affecting the adjuvancy.

Example V

Rectal and Vaginal Immunization Methods

Rectal and vaginal immunization routes were investigated, as follows. Mice were administered 200 μg ovalbumin with 1 μg Toxin A, 25 μg LT, or no adjuvant, at four weekly intervals. Five mice were in each treatment group, and the vaccine was administered in a total volume of 15 μL using a feeding needle while the mice were lightly anesthetized.

TABLE 5

Wilcoxon ranked sums test for statistical comparison of immune responses of animals receiving GST-ARU as a mucosal adjuvant compared to immune responses of animals receiving antigen alone or antigen + LT

| compartment: | | Serum IgA | Serum IgG | Salivary IgG | Salivary IgA | fecal IgA | fecal IgG | vaginal IgG | vaginal IgA |
|---|---|---|---|---|---|---|---|---|---|
| GST-ARU v | OVA alone | 0.009 | 0.009 | 0.009 | 0.009 | 0.009 | 0.0088 | 0.009 | 0.0278 |
| GST-ARU v | OVA + LT | 0.2506 | 0.3472 | 0.2963 | 0.6015 | 0.2506 | 0.754 | 0.1172 | 0.4647 |

After the final immunization, samples of serum and mucosal secretions were taken for measurement of anti-ovalbumin Other embodiments are within the following claims.

What is claimed is:

1. A method of inducing an immune response to an antigen in a mammal that is protective or therapeutic against infection, said method comprising administering to said mammal an adjuvant consisting of (a) an enterotoxin of a bacterium of the genus Clostridium, or (b) a polypeptide comprising the carbohydrate-binding domain of a clostridial enterotoxin and an antigen wherein said antigen is distinct from (a) or (b).

2. The method of claim 1, wherein said antigen and said adjuvant are administered to a mucosal surface of said mammal.

3. The method of claim 2, wherein said mucosal surface is intranasal.

4. The method of claim 2, wherein said mucosal surface is oral.

5. The method of claim 2, wherein said mucosal surface is rectal.

6. The method of claim 2, wherein said mucosal surface is in the genitourinary tract.

7. The method of claim 6, wherein said mucosal surface is vaginal.

8. The method of claim 1, wherein said bacterium is selected from the group consisting of *Clostridium difficile, Clostridium sordellii*, and *Clostridium novyi.*

9. The method of claim 1, wherein said bacterium is *Clostridium difficile.*

10. The method of claim 1, wherein said adjuvant is *Clostridium difficile* Toxin A.

11. The method of claim 1, wherein said adjuvant is *Clostridium difficile* Toxin B.

12. The method of claim 1, wherein said antigen is administered with *Clostridium difficile* Toxin A or a polypeptide comprising the carbohydrate-binding domain of a clostridial Toxin A, and *Clostridium difficile* Toxin B.

13. The method of claim 1, wherein said adjuvant is a component of a fusion protein.

14. The method of claim 13, wherein said fusion protein comprises said antigen.

15. The method of claim 1, wherein said immune response is protective against infection.

16. The method of claim 1, wherein said immune response is therapeutic.

17. The method of claim 1, wherein said immune response is in the genitourinary tract.

18. The method of claim 1, wherein said immune response is in the gastrointestinal tract.

19. The method of claim 1, wherein said antigen is a polypeptide antigen.

20. The method of claim 19, wherein said polypeptide antigen comprises *Helicobacter pylori* urease.

21. A method of inducing an immune response to *Helicobacter pylori* urease in a mammal that is protective or therapeutic against Helicobacter infection, said method comprising administering to a mucosal surface of said mammal *Helicobacter pylori* urease and an adjuvant selected from (a) an enterotoxin of a bacterium of the genus Clostridium, and (b) a polypeptide comprising the carbohydrate-binding domain of a clostridial enterotoxin.

* * * * *